United States Patent [19]

Schnurr et al.

[11] Patent Number: 5,789,621
[45] Date of Patent: Aug. 4, 1998

[54] PREPARATION OF AMINES AND AMINONITRILES

[75] Inventors: Werner Schnurr, Herxheim; Guido Voit, Schriesheim; Klemens Flick, Herxheim; Rolf-Hartmuth Fischer, Heidelberg, all of Germany

[73] Assignee: BASF Aktiengesellschaft, Ludwigshafen, Germany

[21] Appl. No.: 693,983

[22] Filed: Aug. 8, 1996

[51] Int. Cl.[6] ................................ C07C 209/02
[52] U.S. Cl. .................. 564/490; 564/448; 564/491; 564/492; 564/493
[58] Field of Search .................... 564/448, 490, 564/491, 492, 493

[56] References Cited

U.S. PATENT DOCUMENTS

| | | | |
|---|---|---|---|
| 3,869,523 | 3/1975 | Suggitt et al. | 260/668 R |
| 4,440,667 | 4/1984 | Baird, Jr. et al. | 502/53 |
| 4,520,118 | 5/1985 | Gane et al. | 502/53 |
| 4,727,196 | 2/1988 | MacApline et al. | 568/391 |
| 5,626,451 | 5/1997 | Hearn et al. | 564/490 |

*Primary Examiner*—Brian M. Burn
*Attorney, Agent, or Firm*—Keil & Weinkauf

[57] ABSTRACT

A process for preparing an $NH_2$-containing compound by hydrogenating a compound containing at least one unsaturated carbon-nitrogen bond with hydrogen in the presence of a catalyst at temperatures not below room temperature and elevated hydrogen partial pressure in the presence or absence of a solvent which process includes the following steps:

a) using a catalyst comprising a cobalt- and/or iron-containing catalyst, and
b) after the conversion based on the compound to be hydrogenated and/or the selectivity based on the desired product has or have dropped below a defined value or the amount of an unwanted by-product has risen beyond a defined value, interrupting the hydrogenation by stopping the feed of the compound to be hydrogenated and of the solvent, if used,
c) treating the catalyst at from 150° to 400° C. with hydrogen using a hydrogen pressure within the range from 0.1 to 30 MPa and a treatment time within the range from 2 to 48 h, and
d) subsequently continuing the hydrogenation of the compound containing at least one unsaturated carbon-nitrogen bond.

6 Claims, No Drawings

5,789,621

PREPARATION OF AMINES AND AMINONITRILES

BACKGROUND OF THE INVENTION

The present invention relates to an improved process for preparing an $NH_2$-containing compound by hydrogenating a compound containing at least one unsaturated carbon-nitrogen bond with hydrogen in the presence of a catalyst at temperatures not below room temperature and elevated hydrogen partial pressure in the presence or absence of a solvent.

The present invention further relates to a process for preparing specifically 6-aminocapronitrile (ACN) and hexamethylenediamine (HMD), a process wherein the hydrogenation of compounds containing at least one unsaturated carbon-nitrogen bond is carried out in suspension or in a fixed-bed reactor in a downflow or upflow process, and a process for regenerating cobalt- and/or iron-containing catalysts.

DESCRIPTION OF RELATED ART

The hydrogenation of unsaturated carbon-nitrogen bonds with hydrogen is described for example in Houben-Weyl, Vol. 11/1 (nitrogen compounds II, amines), pages 545–574, 4th edition, 1957.

U.S. Pat. No. 2,257,814 discloses a process for preparing aminonitriles from dinitriles by conducting the hydrogenation in the liquid phase in the presence of cobalt- and optionally iron-containing catalysts. Furthermore, DE-A 848,654 describes the partial hydrogenation of adiponitrile (AND) to ACN in the presence of fixed-bed catalysts based on copper/cobalt/zinc and iron-cobalt spinels. DE-A 954,416 describes the use of cobalt on silica gel as a catalyst for preparing aminonitriles and diamines by hydrogenation of dinitriles with hydrogen. DE-A 4,235,466 describes a process for preparing cycloaliphatic and aliphatic aminonitriles by catalytic hydrogenation in the presence of a catalyst prepared from iron sponge.

The cobalt- and iron-containing catalysts used in the hydrogenation of nitriles and imines lose activity in long runs and therefore have to be replaced with new catalysts once certain limits have been reached in respect of conversion and/or selectivity or by-product level.

The regeneration of catalysts coated with carbonaceous deposits is generally effected by burning off the organic coatings with nitrogen-air mixtures (*Chem. Eng. Sci.* 46 (1991), 11–21). However, this method can be used only with catalysts which remain mechanically stable on reaction with air. Supported catalysts having a stable structure of oxidic material, such as $SiO_2$, $Al_2O_3$, $TiO_2$, can be successfully regenerated by this method. For instance, GB-A 2,284,163 describes the regeneration of a supported catalyst with Pt, Pd, Ru, Rh, Os, Ir or Ni by treatment with a gas containing at least chlorine and oxygen.

Catalysts with very high metal contents become damaged on burning off the organic deposits with air, altering their mechanical properties (see EP-A 61,042, for example).

It is known from the *Journal of Catalysis* 143 (1993), 187–200, that a nickel catalyst (25% by weight of Ni on $SiO_2$) which is used for the hydrogenation of acetonitrile in the gas phase can be regenerated by treatment with hydrogen at temperatures above 200° C.

The cited references do not reveal whether it is also possible to regenerate cobalt- and/or iron-containing catalysts under these conditions.

SUMMARY OF THE INVENTION

It is an object of the present invention to provide a process whereby it is possible to regenerate the cobalt- and iron-containing catalysts used in the hydrogenation of a compound containing at least one unsaturated carbon-nitrogen bond in a simple way, without incurring long shutdown times during the regeneration of the catalysts. More particularly, the object is to raise catalyst activity in respect of conversion and selectivity in the hydrogenation of the compound containing at least one unsaturated carbon-nitrogen bond as closely as possible back to the level of the unused catalyst.

We have found that these objects are achieved by a process for preparing an $NH_2$-containing compound by hydrogenating a compound containing at least one unsaturated carbon-nitrogen bond with hydrogen in the presence of a catalyst at temperatures not below room temperature and elevated hydrogen partial pressure in the presence or absence of a solvent, which comprises a) using a catalyst comprising a cobalt- and/or iron-containing catalyst, and b) after the conversion based on the compound to be hydrogenated and/or the selectivity based on the desired product has or have dropped below a defined value or the amount of an unwanted by-product has risen beyond a defined value, interrupting the hydrogenation by stopping the feed of the compound to be hydrogenated and of the solvent, if used, c) treating the catalyst at from 150° to 400° C. with hydrogen using a hydrogen pressure within the range from 0.1 to 30 MPa and a treatment time within the range from 2 to 48 h, and d) subsequently continuing the hydrogenation of the compound containing at least one unsaturated carbon-nitrogen bond.

We have also found a process wherein compounds containing at least one unsaturated carbon-nitrogen bond are hydrogenated in suspension or in a fixed-bed reactor in a downflow or upflow process; a process for preparing specifically 6-aminocapronitrile (ACN) and hexamethylenediamine (HMD); and also a process for regenerating cobalt- and iron-containing catalysts.

DESCRIPTION OF PREFERRED EMBODIMENTS

According to the invention, the starting compounds used are compounds containing at least one unsaturated carbon-nitrogen bond, such as a carbon-nitrogen double or triple bond. Preference is given to using a $C_4$–$C_8$-alkylnitrile or -dinitrile such as butanenitrile, pentanenitrile, hexanenitrile, heptanenitrile, octanenitrile, butanedinitrile (adiponitrile, short ADN), pentanedinitrile, hexanedinitrile, heptanedinitrile and octanedinitrile, especially adiponitrile, particularly preferably terminal $C_4$–$C_8$-dinitriles such as 1,4-dicyanobutane (adiponitrile), 1,5-dicyanopentane, 1,6-dicyanohexane, 1,7-dicyanoheptane and 1,8-dicyanooctane, especially adiponitrile, $C_5$–$C_8$-cycloalkylnitriles or -dinitriles such as cyclopentanecarbonitrile, cyclohexanecarbonitrile, cycloheptanecarbonitrile, cyclooctanecarbonitrile, cyclopentanedicarbonitrile, cyclohexanedicarbonitrile, and also aminonitriles containing from 4 to 8 carbon atoms, preferably α,ω-aminonitriles such as 5-aminovaleronitrile and 6-aminocapronitrile (ACN), especially ACN.

The nitriles, dinitriles and aminonitriles may also carry other functional groups as long as they do not impair the hydrogenation or their simultaneous or partial hydrogenation is desired. Examples are $C_1$–$C_4$-alkyl, aryl, especially phenyl, $C_5$–$C_8$-cycloalkyl, aminoalkyl, N-alkylaminoalkyl, N-(cyanomethyl)aminoalkyl and imino (C=NH, C=NR), preferably imino.

Particularly preferred compounds are ADN, ACN, 3-cyano-3,5,5-trimethylcyclohexylimine, NC—$(CH_2)_2$—N(H)—$(CH_2)_2$—CN, NC—$(CH_2)_2$—N(H)—$(CH_2)_2$—N(H)—$(CH_2)_2$—CN and 1-cyano-2-aminoethane.

The cobalt and/or iron catalysts can be used without support, especially for a fixed-bed or suspension process, for example in the form of Raney catalysts or in other customary unsupported forms. The unsupported forms may contain small (compared to the high content of active components) amounts of additions. These additions may have favorable effects on either the catalytic activity and/or selectivity, or on properties such as hardness, abrasion and chemical or thermal stability of the catalyst. The total amount of additions is generally from 0 to 20 wt %, based on the amount of active component. Examples of additions are oxides, phosphates and sulfates of alkali metal and alkaline earth metal compounds, thermally stable oxides such as $SiO_2$, $Al_2O_3$, $TiO_2$ and $ZrO_2$, and other transition metal oxides. Use in the form of a supported catalyst is also possible. The support used may typically be alumina, silica, activated carbons, titania and zirconia. In supported catalysts, the level of cobalt and/or iron relative to support is generally within the range from 3 to 95, preferably from 30 to 95%, by weight, depending on whether only one or both of cobalt and iron are present.

The catalysts can also be modified, if desired, with metals of group VIB (Cr, Mo, W), VIII of the periodic table of the elements (Ru, Os, Rh, Ir, Pd, Pt) and also copper, manganese and rhenium, in which case the cobalt and/or iron content of the catalyst is generally within the range from 50 to 99.9, preferably from 80 to 99%, by weight, based on the active components (cobalt and/or iron+modifier).

Furthermore, the catalysts may be modified with a compound based on an alkali metal or an alkaline earth metal such as lithium, sodium, potassium, rubidium, cesium, magnesium, calcium, strontium and barium, especially cesium. It is customary to use a weight ratio within the range from 0 to 5, preferably from 0.1 to 3%, by weight of alkali metal or alkaline earth metal, based on mass of cobalt and iron (one of which need not be present).

Preferred catalysts are unsupported iron and cobalt catalysts having an iron and/or cobalt content of at least 60% by weight, based on the mass of cobalt and/or iron and any modifier, if present.

Iron catalysts, which are chiefly used in ammonia synthesis, the Fischer-Tropsch reaction or as dehydrogenation catalyst for making styrene from ethylbenzene, may be prepared in various ways described in the literature. For instance, iron catalysts can be prepared from naturally occurring iron oxides such as hematite or magnetite or metallurgically produced (by oxidation) iron (see *Ullmann's Encyclopedia of Industrial Chemistry*, 5th Ed., Vol. A2, pages 169–172). Modifiers (also known as promoters) are customarily incorporated by conjoint melting of the oxides or applied to the inner surface by subsequent impregnation of the iron oxides. However, the iron oxide precursor may also be obtained by precipitation (see for example B. E. Leach, *Applied Industrial Catalysis*, 2 (1983), 177–180) or coprecipitation onto inert oxidic materials from aqueous iron salt solutions as carbonates or hydroxides. These precursors may be brought into a technically usable form in a conventional manner by tableting or extrusion (A. B. Stiles, *Catalyst manufacture*, New York 1983, pages 137–138, or M. Sittig, *Catalyst Manufacture, Recovery and Use*, 1972, Noyes data corporation, pages 217–221).

A further way of preparing iron catalysts is, for example, the thermal decomposition of iron cyanides to iron carbides and iron nitrides, which can generally be converted into alpha-iron by further heating (see *Ullmann's Encyclopedia of Industrial Chemistry*, 5th Ed., Vol. A2, pages 169–172).

Cobalt catalysts can be prepared by impregnating a ceramic support with aqueous or organic solutions of a cobalt-containing compound. The impregnation can be carried out on the ready-produced extrudate of the support or else on the support powder. If the ceramic support is used as powder, the cobalt-impregnated powder is customarily shaped, for example by extrusion or tableting, preferably after calcination.

If an impregnating step has failed to put sufficient cobalt on the support, for example because of the solubility of the cobalt salts used or the surface area of the support, it is possible, from observations to date, to repeat the impregnating until the desired amount of cobalt has been applied, in which case the resulting mass is dried and calcined after each impregnating step before the next impregnation is carried out.

It is also possible to prepare cobalt-containing catalysts by precipitation from aqueous or organic solution, in which case the modifiers (or promoters) are customarily coprecipitated or may be applied subsequently by impregnation. It is preferred to precipitate cobalt hydroxide or the corresponding carbonate or other sparingly soluble cobalt compounds. After precipitation, it is customary to dry the precipitate and then process the dried mass, for example by extrusion or tableting, although, if desired, it is possible to precede the shaping into extrudates or tablets with a calcination at temperatures within the range from 200° to 700° C. in order that certain, desirable solid-state phases may be obtained.

Before use as hydrogenation catalysts, the cobalt oxide and/or iron oxide precatalysts are advantageously reduced to the corresponding metals by means of a hydrogen treatment, in which case, in general, an oxide content of not more than 10% by weight, preferably of not more than 5% by weight, particularly preferably of not more than 1% by weight, based on the total mass of metal and oxide, is preferable from experience to date. This reduction of the oxide-containing materials to the corresponding active catalyst masses can be carried out under atmospheric or superatmospheric pressure at temperatures from 200° C. in a conventional manner.

The hydrogenations can be carried out in upflow, downflow or suspension.

When the reaction is carried out in a suspension, it is customary to choose temperatures within the range from 40° to 150° C., preferably within the range from 50° to 100° C., particularly preferably within the range from 60° to 90° C.; the pressure is generally chosen to be within the range from 2 to 20, preferably from 3 to 10, particularly preferably from 4 to 9, MPa. The residence times are essentially dependent on the desired yield, selectivity and the desired conversion; customarily, the residence time is selected so as to maximize the yield, for example within the range from 50 to 275, preferably within the range from 70 to 200, min.

In the suspension process, the solvent used is preferably ammonia, amines, diamines and triamines having from 1 to 6 carbon atoms such as trimethylamine, triethylamine, tripropylamine and tributylamine or alcohols, especially methanol and ethanol, particularly preferably ammonia. It is advantageous to use a concentration of the compound to be hydrogenated within the range from 10 to 90, preferably from 30 to 80, particularly preferably from 40 to 70%, by weight, based on the sum of compound to be hydrogenated and solvent.

The amount of catalyst used is generally within the range from 1 to 50, preferably from 5 to 20%, by weight, based on the amount of compound to be hydrogenated used.

The suspension hydrogenation can be carried out batchwise or, preferably, continuously, generally in the liquid phase.

The hydrogenation may also be carried out batchwise or continuously in a fixed-bed reactor in a downflow or upflow process, in which case it is customary to employ a temperature within the range from 30° to 200° C., preferably within the range from 50° to 150° C., and a pressure generally within the range from 2 to 30, preferably within the range from 3 to 20, MPa. The hydrogenation is preferably carried out in the presence of a solvent, preferably ammonia, amines, diamines and triamines having from 1 to 6 carbon atoms such as trimethylamine, triethylamine, tripropylamine and tributylamine or alcohol, preferably methanol and ethanol, particularly preferably ammonia. In a preferred embodiment, the amount of ammonia used is within the range from 0.5 to 10, preferably from 1 to 6, g per g of compound to be hydrogenated, especially adiponitrile. Preference is given to using a catalyst space velocity within the range from 0.1 to 2.0, preferably from 0.3 to 1.0, kg of the compound to be hydrogenated/l*h, especially adiponitrile/l*h. Here too it is possible to adjust the conversion and hence the selectivity in a specific manner by varying the residence time.

The hydrogenation can be carried out in a customary suitable reactor.

If the reaction is carried out in the gas phase, it is customary to use temperatures within the range from 100° to 250° C., preferably within the range from 160° to 200° C.; the pressure employed is generally within the range from 0.01 to 3, preferably from 0.09 to 0.5, MPa. Furthermore, the molar ratio of hydrogen to compound containing at least one unsaturated carbon-nitrogen bond is generally within the range from 2:1 to 300:1, preferably within the range from 10:1 to 200:1.

In a preferred embodiment, the hydrogenation of ADN is carried out in the presence of ammonia as solvent using fixed-bed catalysts by a process wherein, following the deactivation of the catalyst, ie. a decrease in the conversion of ADN and/or selectivity based on ACN below a defined value, first the feed of adiponitrile and ammonia is switched off, then the temperature is brought to 200°–250° C., and subsequently the catalyst is treated for from ten to twenty hours with from 200 to 800, preferably from 500 to 700, especially 600, 1 of hydrogen/l of cat.×h. Thereafter the temperature is customarily brought back down to reaction temperature and the hydrogenation is continued.

Prior to starting the regeneration, it is preferable to remove the hydrogenation mixture still present in the reactor. It may be advantageous to wash the catalyst before the actual regeneration with the solvent present in the system, especially ammonia. The wash temperature employed is customarily within the range from 20° to 200° C., especially within the range from 20° to 100° C. It is generally advantageous to carry on the wash for a period of from 2 to 24 hours.

According to the invention, the regeneration of the catalyst is carried out at temperatures within the range from 150° to 400° C., preferably within the range from 180° to 350° C., especially within the range from 200° to 300° C., using a hydrogen pressure within the range from 0.1 to 30 MPa, preferably within the range from 0.1 to 20 MPa. A continuous process is customarily carried out with the hydrogen rate within the range from 100 to 1500, preferably within the range from 200 to 1000, 1 of hydrogen/l of reactor volume× hour.

The process of the invention makes it possible to achieve distinct improvements in the life and space-time yield of cobalt- and/or iron-containing catalysts in the hydrogenation of compounds containing at least one unsaturated carbon-nitrogen bond, especially in the hydrogenation of adiponitrile to aminocapronitrile and hexamethylenediamine (nylon 6 and nylon 66 intermediates).

EXAMPLES

Example 1

Preparation of an unsupported cobalt catalyst

20% strength by weight sodium carbonate solution was added a little at a time to an aqueous solution of cobalt nitrate, manganese nitrate and phosphoric acid in water containing 10% by weight of cobalt (calculated on the basis of cobalt nitrate), 0.55% by weight of manganese (calculated from the amount of manganese nitrate) and 0.45% by weight of $H_3PO_4$ at 50° C. in such a way as to always produce a pH of 6 on completion of the addition of the sodium carbonate solution; the corresponding carbonates were precipitated. On completion of the precipitation, discernible from the fact that the established pH of 6 did not change, further sodium carbonate solution was added until a pH of 7.5 was obtained. The resulting precipitate was washed nitrate and sodium-free by washing the precipitate with water until a final conductivity of 20 μsiemens was obtained and, according to Merckoquant® test strips for nitrate (from Merck), the nitrate content of the solution was less than 0.02% by weight. The precipitate thus washed was suspended in water and sprayed into a spray-tower (inlet temperature=550° C.). The sprayed material was dried at 500° C., mulled and shaped in an extruder into extrudates 4 mm in diameter and 1 cm in length. The extrudates were dried at from 100° to 120° C., and calcined at 900° C. for 1 h. The calcined product had a composition of 90% by weight of CoO, 5% by weight of $Mn_2O_3$, 3% by weight of $P_2O_5$ and 2% by weight of $Na_2O$. The extrudates thus obtained were reduced at 320° C. in a stream of hydrogen for 16 h and passivated at room temperature with a nitrogen-air mixture (5% by volume of air, 95% by volume of nitrogen).

Example 2

Preparation of an unsupported iron catalyst

The method described in *Catalyst Manufacture*, A. B. Stiles, T. A. Koch (1995), pages 167/68, was followed to melt a mixture of iron oxide (magnetite) with the promoters $Al_2O_3$, $K_2CO_3$ and calcium carbonate at from 1600° to 2000° C. The melt was subsequently cooled and comminuted. The material obtained (catalyst in the oxidic state) had the following composition: 1.1% by weight of $K_2O$, 3.0% by weight of $Al_2O_3$, 2.3% by weight of CaO, remainder FeO and $Fe_2O_3$. To obtain a usable catalyst, the material obtained was treated at 450° C. with hydrogen at 3 MPa for 32 h and then passivated at room temperature with a nitrogen/air mixture (5% by volume of air, 95% by volume of nitrogen). The ratio of mass of metals to mass of oxides ("degree of reduction") was 9:1.

Example 3

Fixed-bed hydrogenation in the liquid phase

A tubular reactor 2 m in length and 2.5 cm in internal diameter was packed with 750 ml (1534 g) of the passivated catalyst of Example 1. The passivated catalyst was then activated over 48 h in a stream of nitrogen (500 l/h) under atmospheric pressure by raising the temperature from 30° C. to 280° C. (during which time previously unconverted CoO was reduced to Co).

After lowering the reactor inlet temperature to 45° C. and the reactor outlet temperature to 85° C., the reactor was supplied under a total pressure of 20 MPa with a mixture of 400 ml/h of adiponitrile, 600 ml/h of ammonia and 500 l/h of hydrogen. In addition, to remove the heat, about four times the feed quantity (4.2 l/h) was recycled via a heat exchanger. Under these conditions, the adiponitrile conversion was 70%. The initial reaction mixture contained 30% by weight of ADN, 35% by weight of ACN and 34.5% of HMD (ACN selectivity: 50%, ACN+HMD selectivity: >99%). Following a run of 3,600 h, the ACN selectivity dropped from an initial 50% to 23% while the conversion remained unchanged.

Thereafter the dinitrile and ammonia feed was switched off and the catalyst regenerated in the reactor over 12 hours at 200° C. and a total pressure of 200 bar (at 500 l/h of hydrogen). A renewed startup under identical conditions (see above) produced an increase in the selectivity to 50%; that is, the catalyst had been restored to its initial selectivity.

Example 4

Fixed-bed hydrogenation in the liquid phase

A tubular reactor 2 m in length and 2.5 cm in internal diameter was packed with 800 ml (1598 g) of the passivated catalyst of Example 1. The catalyst was then activated over 48 h under atmospheric pressure in a stream of hydrogen (500 l/h) by raising the temperature from 30° C. to 320° C. (in which period residual CoO was reduced to Co).

After lowering the reactor inlet temperature to 120° C. and the reactor outlet temperature to 140° C., the reactor was supplied at 25 MPa in the downflow direction with a mixture of 180 ml/h of 3-cyano-3,5,5-trimethylcyclohexylimine, 1700 ml/h of ammonia and 500 ml/h of hydrogen. Under these conditions the imine conversion was 100%. The yield of 3-aminomethyl-3,5,5-trimethylcyclohexylamine was 94% (selectivity: 94%). 3-Cyano-3,5,5-trimethylcyclohexylamine was a hydrogenation intermediate and hence an indicator of the catalyst activity. The concentration of this compound rose from an initial 0 ppm to 1500 ppm (based on the reaction mixture) after 5700 h, so that catalyst regeneration appeared to be necessary for product specification reasons.

Thereafter the nitrile and ammonia feed was switched off and the catalyst regenerated in the reactor over 24 h at 300° C. and a total pressure of 25 MPa (at 500 l/h of hydrogen). A renewed startup under identical conditions as above produced a drop in the intermediate concentration to 200 ppm; that is, the catalyst had been almost completely restored to its initial activity.

Example 5

Fixed-bed hydrogenation in the liquid phase

A tubular reactor 7 m in length and 10.5 cm in internal diameter was packed with 60 l (130 kg) of the catalyst obtained in Example 2 (degree of reduction 9:1) and then the catalyst was activated over 72 h at 370° C. and a total pressure of 15 MPa (reducing the remaining iron oxide to iron) by first passing nitrogen through the reactor and then replacing the nitrogen step by step with hydrogen during the first 24 h.

After lowering the reactor inlet temperature to 110° C. and the reactor outlet temperature to 135° C., the reactor was supplied under a total pressure of 25 MPa with a mixture of 30 kg/h of ADN, 50 l/h of liquid ammonia and 40 standard $m^3/h$ of hydrogen. In addition, to remove the heat, five times the feed quantity (400 l/h) was recirculated via a heat exchanger (giving a recycle stream temperature at the reactor inlet of 110° C). Under these conditions the ADN conversion was 70%. The initial reaction mixture contained 30% by weight of ADN, 35% by weight of ACN and 34.5% by weight of HMD (ACN selectivity: 50%, ACN+HMD selectivity: >99%). After 800 h the catalyst was specifically deactivated by switching off the feeds without rinsing.

For regeneration, the catalyst was treated in the reactor initially with nitrogen (80 $m^3/h$) at a temperature within the range from 200° to 250° C. and a pressure of 15 MPa, for 24 h. This was followed by heating to 270° C. and stepwise replacement of the nitrogen (80 $m^3/h$) with hydrogen over 5 h. During the replacement of nitrogen with hydrogen the temperature was likewise increased stepwise to 380° C. Finally the reactor was maintained at a temperature within the range from 350° to 380° C. and a hydrogen pressure of 20 MPa for 24 h. On a renewed startup under the same conditions as indicated above the selectivity of the catalyst was back to its initial level.

We claim:

1. A process for preparing an $NH_2$-containing compound by hydrogenating a compound containing at least one unsaturated carbon-nitrogen bond with hydrogen in the presence of a catalyst at temperatures not below room temperature and elevated hydrogen partial pressure in the presence or absence of a solvent, which comprises a) using a catalyst comprising a cobalt- and/or iron-containing catalyst, and b) after the conversion based on the compound to be hydrogenated and/or the selectivity based on the desired product has or have dropped below a defined value or the amount of an unwanted by-product has risen beyond a defined value, interrupting the hydrogenation by stopping the feed of the compound to be hydrogenated and of the solvent, if used, c) treating the catalyst at from 150° to 400° C. with hydrogen using a hydrogen pressure within the range from 0.1 to 30 MPa and a treatment time within the range from 2 to 48 h, and d) subsequently continuing the hydrogenation of the compound containing at least one unsaturated carbon-nitrogen bond.

2. A process as defined in claim 1, wherein the compound containing at least one unsaturated carbon-nitrogen bond is a $C_4$–$C_8$-alkylnitrile, a $C_5$–$C_8$-cycloalkylnitrile, a $C_4$–$C_8$-alkyldinitrile or a $C_5$–$C_8$-cycloalkyldinitrile.

3. A process as defined in claim 1, wherein adiponitrile is used to obtain 6-aminocapronitrile and hexamethylenediamine.

4. A process as defined in claim 1, wherein the hydrogenation of the compound containing at least one unsaturated carbon-nitrogen bond is carried out in suspension at a temperature within the range from 40° to 150° C. and at a pressure within the range from 2 to 20 MPa.

5. A process as defined in claim 1, wherein the hydrogenation of the compound containing at least one unsaturated carbon-nitrogen bond is carried out in a fixed-bed reactor in a downflow or upflow process at a temperature within the range from 30° to 200° C. and at a pressure within the range from 2 to 30 MPa.

6. A process for regenerating a cobalt- and/or iron-containing catalyst, which comprises treating the catalyst with hydrogen at from 150° to 400° C. using a hydrogen pressure within the range from 0.1 to 30 MPa and a treatment time within the range from 2 to 48 h.

* * * * *

UNITED STATES PATENT AND TRADEMARK OFFICE
CERTIFICATE OF CORRECTION

PATENT NO.: 5,789,621

DATED: August 4, 1998

INVENTOR(S): SCHNURR et al.

It is certified that error appears in the above-identified patent and that said Letters Patent is hereby corrected as shown below:

On the title page,

Insert the following foreign priority information on the cover sheet as follows:

--[30]  Foreign Application Priority Data
Jul. 31, 1996   [DE]   Germany ............ 196 30 788.0--.

Signed and Sealed this

Fifteenth Day of June, 1999

Attest:

Attesting Officer

Q. TODD DICKINSON

Acting Commissioner of Patents and Trademarks